(12) United States Patent
Ishii et al.

(10) Patent No.: US 6,672,760 B2
(45) Date of Patent: Jan. 6, 2004

(54) ONBOARD X-RAY CT APPARATUS, CONTAINER FOR MOUNTING X-RAY CT APPARATUS, AND MOTOR VEHICLE FOR MOUNTING X-RAY CT APPARATUS

(75) Inventors: Takahiro Ishii, Utsunomiya (JP); Tatsuro Suzuki, Utsunomiya (JP); Tetsuya Honda, Otawara (JP); Masami Fujieda, Nasu-gun (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 306 days.

(21) Appl. No.: 09/881,694

(22) Filed: Jun. 18, 2001

(65) Prior Publication Data

US 2001/0053203 A1 Dec. 20, 2001

(30) Foreign Application Priority Data

Jun. 19, 2000 (JP) ........................ 2000-182564
Jun. 19, 2000 (JP) ........................ 2000-182566
Mar. 1, 2001 (JP) ........................ 2001-056268

(51) Int. Cl.⁷ ................................ H05G 1/02
(52) U.S. Cl. ..................................... 378/198
(58) Field of Search ................. 378/4, 20, 57, 378/197, 198; 180/14.2; 280/32.7, 423.1, 425.1, 425.2, 456.1, 467, 412, 477, 479.2, 638, 656

(56) References Cited

U.S. PATENT DOCUMENTS 5,754,617 A * 5/1998 Itoh .......................... 378/4

FOREIGN PATENT DOCUMENTS

| JP | 6-154202 | 6/1994 |
| JP | 3027769 | 5/1996 |
| JP | 8-127282 | 5/1996 |
| JP | 2685813 | 8/1997 |

OTHER PUBLICATIONS

Radiological Sciences vol. 37 No. 12 Dec. 25, 1994 p474–475.

* cited by examiner

Primary Examiner—William Oen
(74) Attorney, Agent, or Firm—Oblon, Spivak, McClelland, Maier & Neustadt, P.C.

(57) ABSTRACT

This invention provides an X-ray CT apparatus which can be mounted in a motor vehicle, trailer, or container, including locking mechanisms for locking at least some of the movable portions of the X-ray CT apparatus, detectors for detecting the locking/unlocking states of the locking mechanisms, and a notifying unit for representing the states of the locking mechanisms on the basis of outputs from the detectors. Collision of an unlocked movable portion with its periphery during traveling can be avoided.

21 Claims, 11 Drawing Sheets

ONBOARD X-RAY CT APPARATUS, CONTAINER FOR MOUNTING X-RAY CT APPARATUS, AND MOTOR VEHICLE FOR MOUNTING X-RAY CT APPARATUS

CROSS-REFERENCE TO RELATED APPLICATIONS

This application is based upon and claims the benefit of priority from the prior Japanese Patent Applications No. 2000-182564, filed Jun. 19, 2000; No. 2000-182566, filed Jun. 19, 2000; and No. 2001-056268, filed Mar. 1, 2001, the entire contents of all of which are incorporated herein by reference.

BACKGROUND OF THE INVENTION

The present invention relates to an onboard X-ray CT apparatus which can be mounted in a motor vehicle, trailer, or container, a container for mounting the X-ray CT apparatus, and a motor vehicle for mounting the X-ray CT apparatus.

X-ray CT apparatuses for obtaining the tomographic image of an object to be examined by exposing the object from his/her surroundings to X-rays, measuring the amount of X-rays having passed through the object, and performing image reconstruction processing for the obtained projection data by using a computer are effective for detection of a disease in its early stage and determination of an appropriate therapeutic plan. Further, a so-called X-ray CT apparatus onboard vehicle, e.g., a motor vehicle such as a bus which contains an X-ray CT apparatus is moved to a disaster-stricken area where image diagnosis for the presence/absence of a fracture or an injury to a viscus is done. Such a motor vehicle is also exploited for itinerant diagnosis or group examination in a depopulated area such as a mountainous area.

Recently, the development of helical scanning X-ray CT apparatuses enables photographing in a pectoral region within one breath. Along with this, strong demands have arisen for implementation of an X-ray CT apparatus onboard vehicle which contains a helical scanning X-ray CT apparatus for group examination in order to detect a pectoral disease in its early stage.

A known example of a conventional X-ray CT apparatus onboard vehicle is disclosed in Utility Model Registration No. 3,027,769, and schematically shown in FIG. 1. A gantry 2a and bed 2b of an X-ray CT apparatus are mounted at the center of a large-bus type vehicle 1 in the longitudinal direction. A power supply device 3 and high-voltage generator 4 are installed in the space between a driver's seat 18 at the front portion of the vehicle and the gantry 2a and bed 2b. An X-ray monitor 5 and console 6 are installed at the back portion of the vehicle 1. A doorway 12 and lift device 15 for an object who uses a stretcher or wheelchair are formed in the back wall surface of the vehicle 1. A doorway 13 for an object who can walk by himself/herself is also formed in the backward side wall surface of the vehicle 1.

Other X-ray CT apparatus onboard vehicles are disclosed in Jpn. Pat. Appln. KOKAI Publication Nos. 6-154202 and 8-127282.

In the X-ray CT apparatus onboard vehicle disclosed in Utility Model Registration No. 3,027,769, the power supply device 3 is installed in the same room as the gantry 2a and bed 2b of the X-ray CT apparatus, which impairs safety and gives annoying noise to an object during an examination.

The X-ray CT apparatus disclosed in Jpn. Pat. Appln. KOKAI Publication No. 6-154202 performs X-ray CT photographing while an object sits on a chair, and is not suitable for X-ray CT photographing of a severely wounded object. The X-ray CT apparatus disclosed in Jpn. Pat. Appln. KOKAI Publication No. 8-127282 is an industrial X-ray CT apparatus mounted in a large trailer, and is not suited for itinerate diagnosis or group examination in a depopulated area such as a mountainous area owing to the road situation.

These conventional X-ray CT apparatus onboard vehicles do not consider any protection means for the movable portions of the mounted X-ray CT apparatuses, and the movable portions of the X-ray CT apparatuses may be damaged by vibrations or shocks during traveling of the X-ray CT apparatus onboard vehicle.

In the conventional X-ray CT apparatus onboard vehicles, a CT operation room and the like are designed in accordance with a mounted X-ray CT apparatus, which makes it difficult to exchange the X-ray CT apparatus with another type apparatus upon upgrading the apparatus.

BRIEF SUMMARY OF THE INVENTION

It is an object of the present invention to provide an X-ray CT apparatus suitably mounted in a motor vehicle, trailer, or container.

According to the present invention, there is provided an X-ray CT apparatus which can be mounted in a motor vehicle, trailer, or container, comprising locking mechanism unit for locking at least one of movable portions of the X-ray CT apparatus, detectors for detecting locking states of the locking mechanism unit, and a notifying unit for representing the states of the locking mechanism unit on the basis of outputs from the detectors.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

The present invention can be applied to an X-ray CT apparatus which can be mounted in a motor vehicle, trailer, or container, and a motor vehicle, trailer, or container for mounting the X-ray CT apparatus. A motor vehicle which contains an X-ray CT apparatus will be described.

(First Embodiment)

Figure 1:
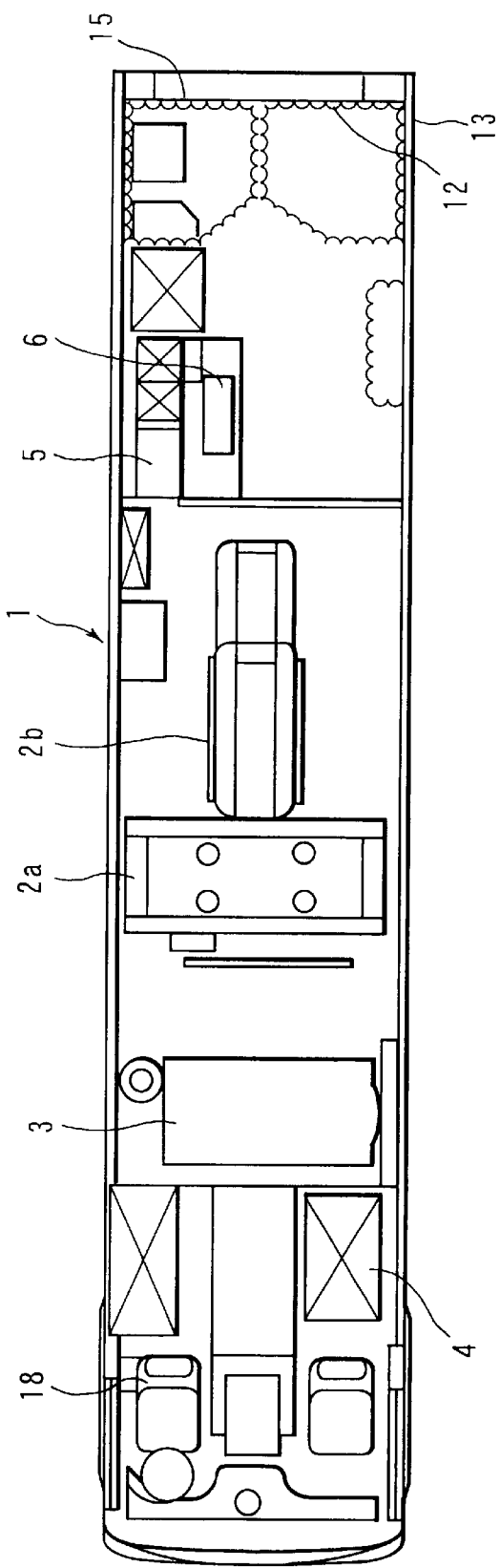
FIG. 1 is a plan view for explaining a conventional X-ray CT apparatus onboard vehicle.
Figure 2:
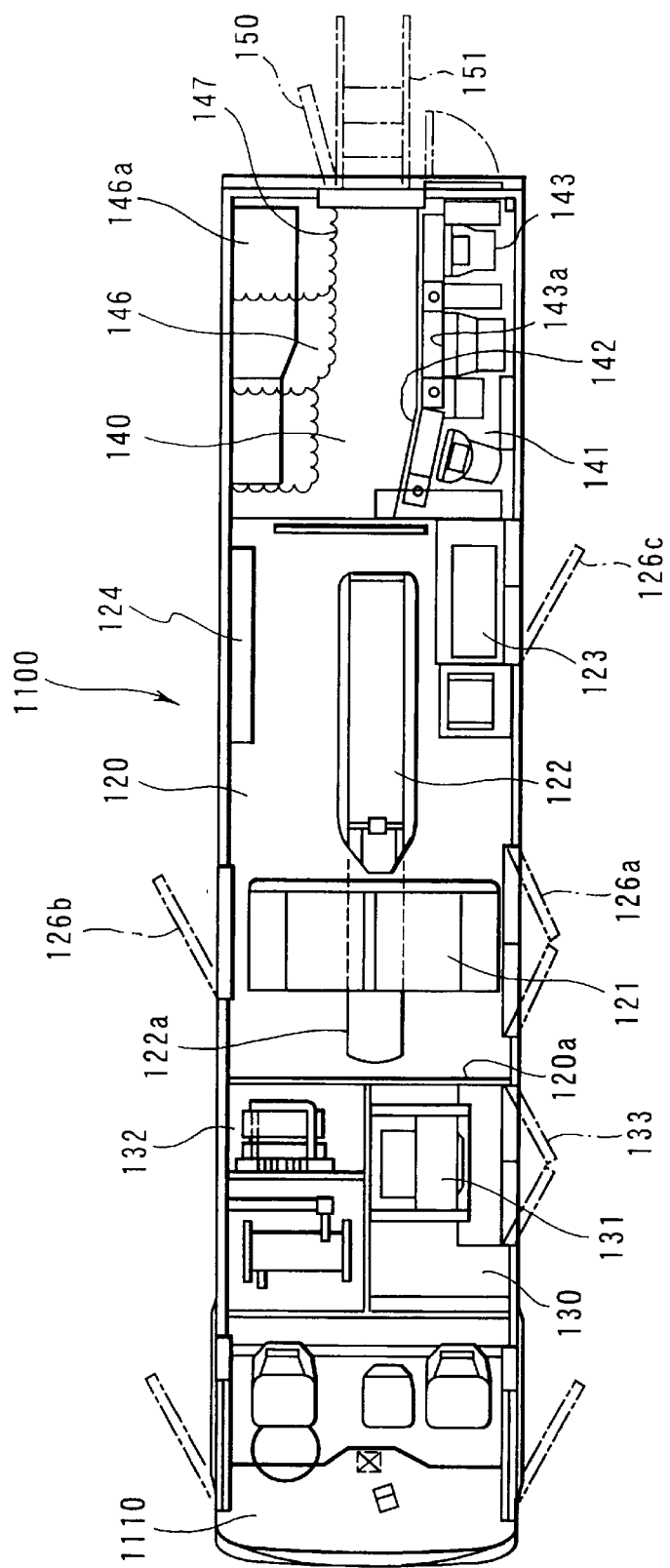
FIG. 2 is a plan view showing an X-ray CT apparatus onboard vehicle according to an embodiment of the present invention.
Figure 3:
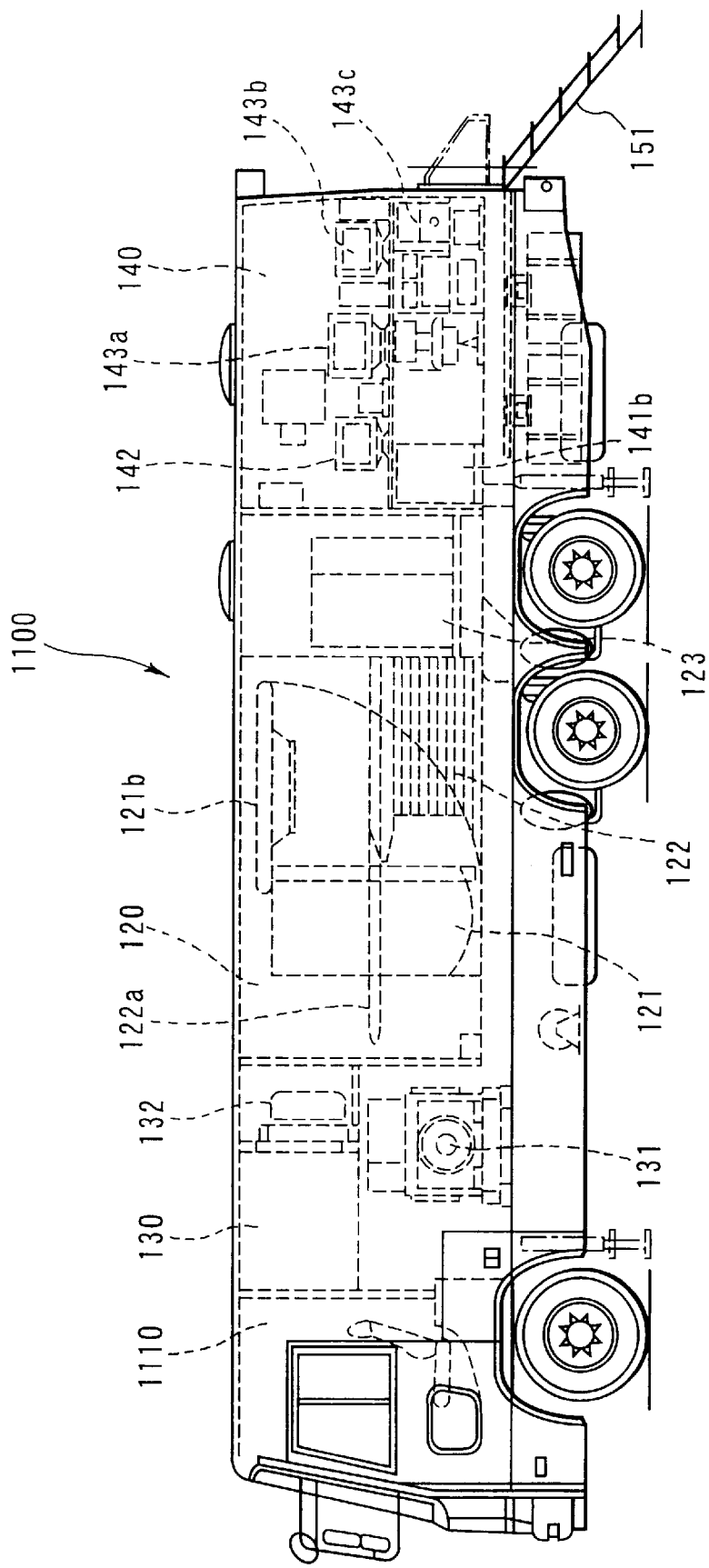
FIG. 3 is a side view of FIG. 2.

FIG. 2 is a plan view showing the overall layout of an x-ray CT apparatus onboard vehicle according to the first embodiment. FIG. 3 is a side view of the X-ray CT apparatus onboard vehicle. In FIG. 2, the ceiling of the vehicle is not illustrated. In an X-ray CT apparatus onboard vehicle 1100 according to the first embodiment, a CT operation room 120 is formed at almost the center of a motor vehicle such as a large bus having a driver's seat 1110 at the front portion. A power supply room 130, part of which has a two-layered structure, is formed between the driver's seat 110 and the CT operation room 120. A staff room 140 is formed after the CT operation room 120. A doorway 150 for an object is formed in the back wall of the motor vehicle so as to communicate with the staff room 140. The staff room 140 also serves as a dressing room for an object.

The CT operation room 120 has the largest space in the motor vehicle where a gantry 121 and bed 122 of an X-ray CT apparatus are installed and fixed to the floor, and an air-conditioning system 123 and switchboard 124 are also installed. In general, the X-ray CT apparatus is constituted by the gantry 121, the bed 122, and a console 141. The console 141 is arranged in the staff room 140, as will be described later.

Figure 4:
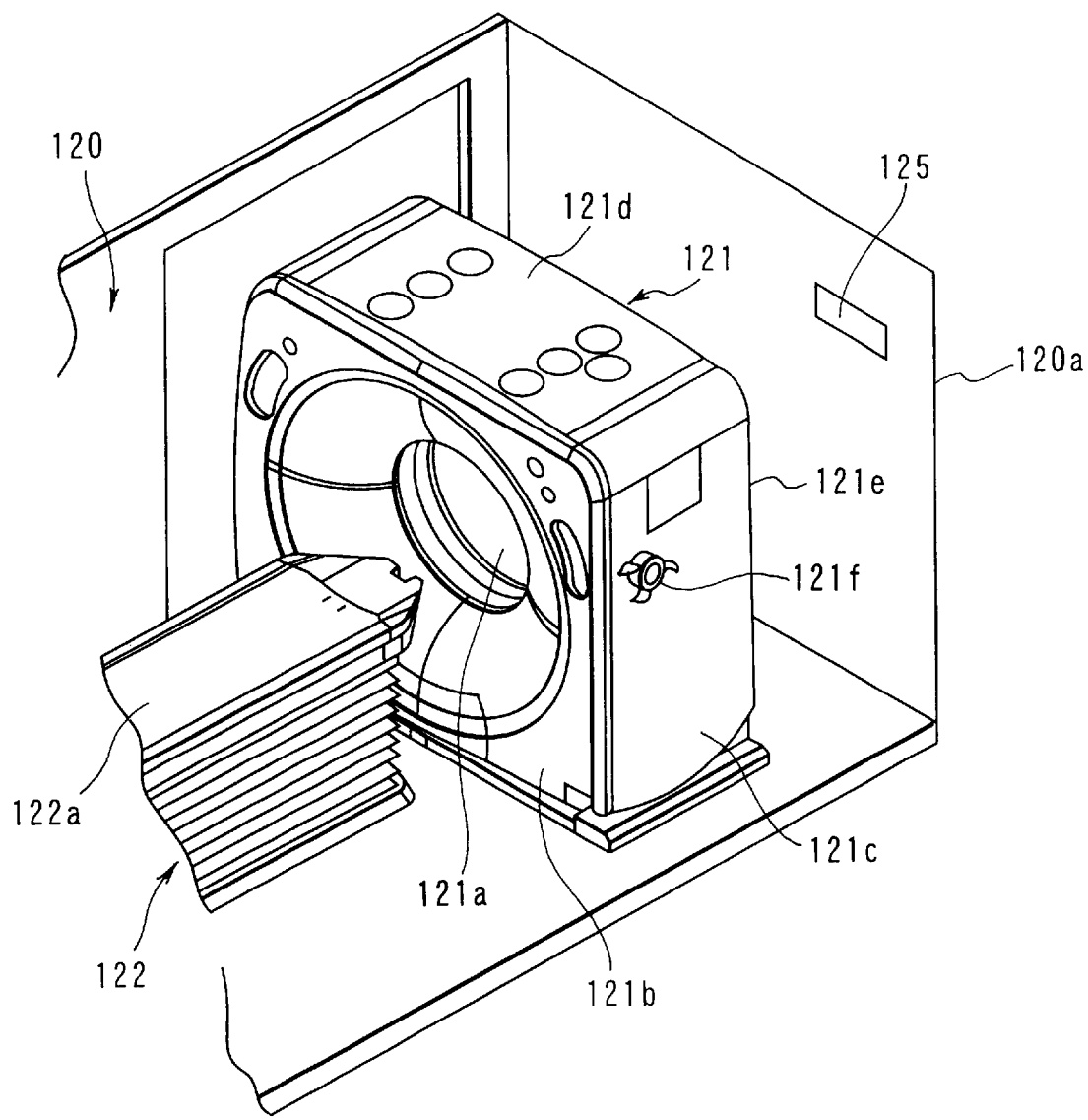
FIG. 4 is a perspective view showing a CT scanner in FIG. 2.

FIG. 4 is an enlarged view showing part of the gantry 121 and bed 122 installed in the CT operation room 120. A through hole 121a serving as a photographing port is formed at the center of the gantry 121, and an object on a top plate 122a of the bed 122 is fed into the photographing port 121a by sliding the top plate 122a. The slide stroke of the top plate 122a to the photographing port 121a can be properly set by the spatial conditions of the CT operation room 120, e.g., the distance between the gantry 121 and a partition wall 120a which partitions the CT operation room 120 from the power supply room 130.

This is because the size of the gantry 121 is supposed to change depending on the type of motor vehicle or the type of X-ray CT apparatus installed in the CT operation room 120. When the CT operation room 120 is small, the top plate 122a which slides is prevented from interfering with partition wall 120a.

To allow an object to easily get on and off the bed 122, the bed 122 is equipped with an interlock circuit so as to move the bed 122 down to almost 35 cm above the floor while the top plate 122a is retracted, and to prevent slide of the top plate 122a unless the bed 122 moves up to a predetermined height.

Although not shown, the gantry 121 has a rotating ring to which an X-ray tube and X-ray detector are attached to face each other via the photographing port 121a. The gantry 121 incorporates a driving unit for driving the rotating ring, a tilt mechanism for tilting the gantry 121, a high-voltage generator for generating a high voltage to be applied to the X-ray tube, and a signal amplifier for amplifying a signal detected by the X-ray detector. The tilt angle of the tilt mechanism can also be properly set in accordance with the spatial conditions of the CT operation room 120 in order not to interfere with the ceiling and partition wall 120a of the CT operation room 120 even if a different type of gantry 121 is installed in the CT operation room 120, similar to the bed 122 and top plate 122a.

The surface of the gantry 121 has a cover, which is divided into a front cover 121b, side cover 121c, upper cover 121d, and back cover 121e. In general maintenance, as shown in FIG. 2, the front cover 121b is opened toward the ceiling of the motor vehicle so as to enable access to an internal device from the front side.

A handle 121f of the tilt locking mechanism projects from the side cover 121c of the gantry 121. The handle 121f of the locking mechanism can be rotated clockwise or counterclockwise to lock the tilting gantry 121 or unlock the gantry 121. Operating the handle 121f can easily switch the gantry 121 between a locking state and an unlocking state. While the X-ray CT apparatus onboard vehicle 1100 travels, the gantry 121 can be locked to suppress collision between the gantry 121 and another portion within a small space, and vibrations which degrade the movable portions of the gantry 121 due to metal fatigue or the like. When the X-ray CT apparatus onboard vehicle 1100 stops at a predetermined position and the X-ray CT apparatus is to operate, the gantry 121 can be easily unlocked.

In photographing by the X-ray CT apparatus, the gantry 121 is tilted to a predetermined angle by the tilt mechanism, as needed. At this time, the gantry 121 is fixed by a brake, which is different from locking operation of the tilt mechanism using the handle 121f as the locking mechanism.

Figure 5:
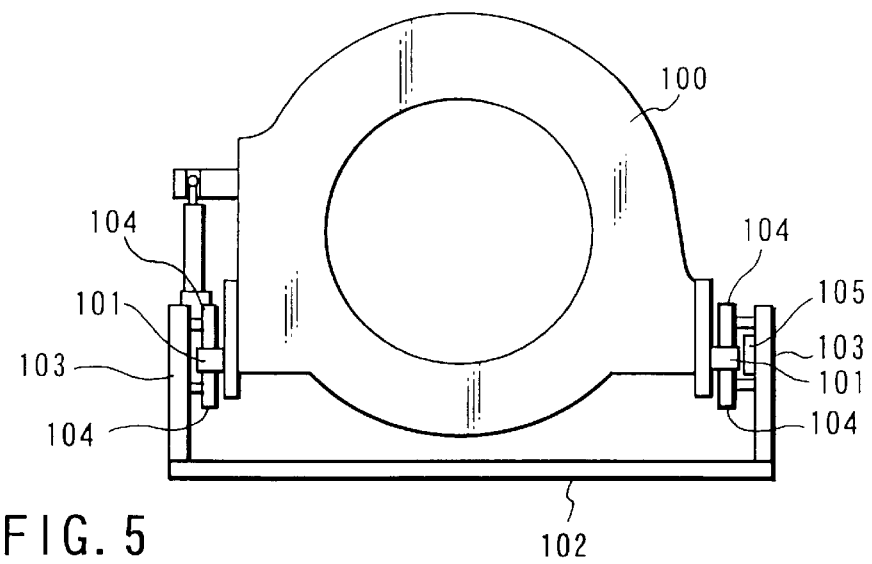
FIG. 5 is a plan view showing the interior of a gantry in FIG. 2.
Figure 6:
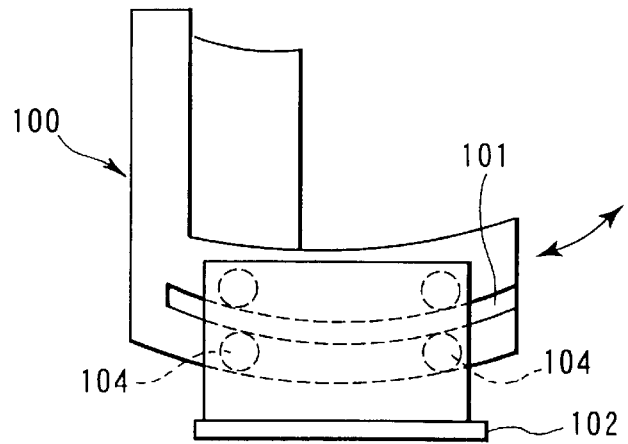
FIG. 6 is a side view showing a tilt mechanism in FIG. 5.
Figure 7:
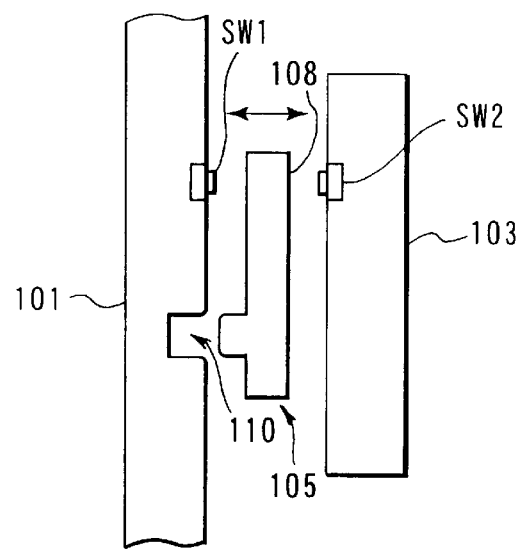
FIG. 7 is a plan view showing a locking mechanism in FIG. 5.

FIGS. 5, 6, and 7 show the tilt locking mechanism. The rotating ring has the X-ray tube and X-ray detector. This rotating ring is rotatably supported by a ring frame 100. Arcuated rails 101 are attached to the right and left sides of the ring frame 100. Each rail 101 is set on rollers 104 pivotally fixed to a side plate 103 of a base stand 102. The rails 101 move on the rollers 104 to tilt the ring frame 100 forward and backward.

Each locking plate 105 is movably held at the gap between the rail 101 and the side plate 103 of the base stand 102. When the handle 121f is rotated clockwise, the locking plate 105 comes close to the rail 101, and when the handle 121f is rotated counterclockwise, the locking plate 105 moves apart from the rail 101 and comes close to the side plate 103. When the locking plate 105 comes into contact with the rail 101, a locking pin 109 of the locking plate 105 fits in a pin hole 110 of the rail 101. Then, the x-ray CT apparatus onboard vehicle 100 is fixed. The position of the pin hole 110 is designed such that the ring frame 100 has a tilt angle of 0°, i.e., stands vertically upon fixing.

When the locking plate 105 moves apart from the rail 101, the locking pin 109 of the locking plate 105 comes out of the pin hole 110 of the rail 101, and the ring frame 100 freely tilts.

A first microswitch SW1 detects a tilt-locking state, and is designed to be turned on when the locking plate 105 comes into contact with the rail 101 and be turned off when the locking plate 105 moves apart from the rail 101. A second microswitch SW2 detects a state wherein the tilt-locking state is completely released, and is designed to be turned on when the locking plate 105 comes into contact with the side plate 103 and be turned off when the locking plate 105 moves apart from the side plate 103. The two switches SW1 and SW2 can accurately detect three states, i.e., a locking state, unlocking state, and intermediate state wherein neither locking or unlocking is completed. The locking state corresponds to the ON state of the first microswitch SW1 and the OFF state of the second microswitch SW2. The unlocking state corresponds to the OFF state of the first microswitch SW1 and the ON state of the second microswitch SW2. The intermediate state corresponds to the OFF states of both the first and second microswitches SW1 and SW2.

Whether the handle 121f is in the locked, unlocked, or intermediate state of the tilt mechanism is displayed on a display 125 so as to prevent the operator from misunderstanding the state at the start of traveling the X-ray CT apparatus onboard vehicle 100 or at the start of operating the X-ray CT apparatus. More specifically, when the first microswitch SW1 is turned on, the display 125 displays that the tilt mechanism is kept locked and a so-called locking mechanism is operating. When the second microswitch SW2 is turned on, the display 125 displays that the tilt mechanism is unlocked and the locking mechanism is kept stopped. When the tilt mechanism is being locked or unlocked or is not reliably locked or unlocked, both the first and second microswitches SW1 and SW2 are OFF. At this time, the display 125 receives a signal via a NOR gate G1 and displays that the locking mechanism is abnormal.

Figure 8:
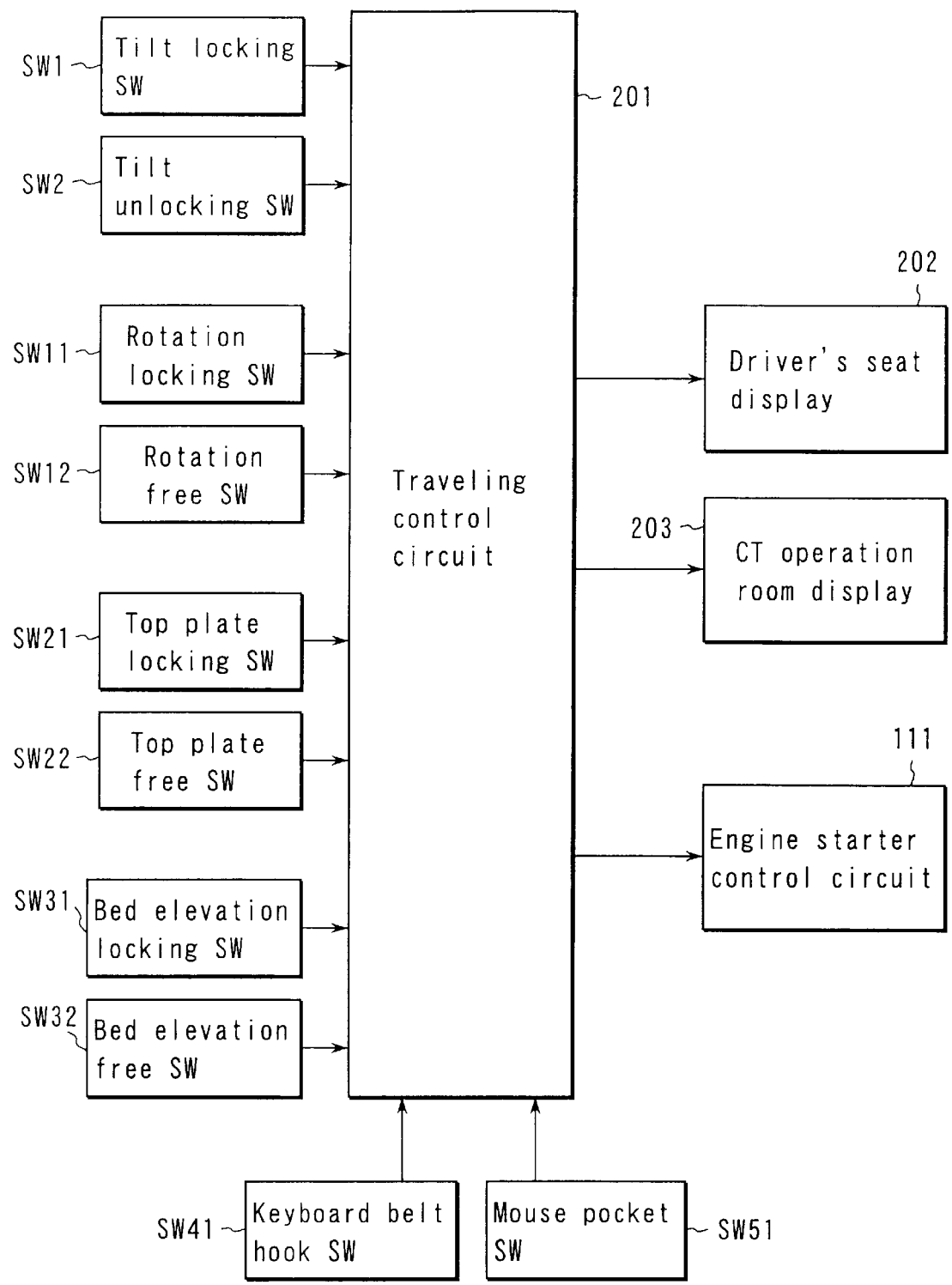
FIG. 8 is a block diagram showing a traveling control system according to the embodiment of the present invention.

As shown in FIG. 8, the display 125 includes a display 202 set at the driver's seat and a display 203 installed in the CT operation room. The display 203 displays the three states of the tilt locking mechanism so as to distinguish them. Similarly, the display 202 at the driver's seat displays the three states of the tilt locking mechanism so as to distinguish them. Note that the display 203 in the CT operation room may display the three states of the tilt locking mechanism so as to distinguish them, and the display 202 may simply display a message "traveling is ready." upon completely locking the tilt locking mechanism because the driver needs information about whether traveling is enabled or disabled.

Instead of displaying a locking-state message, the message may be output by sounds or may be displayed and output by sounds.

The first embodiment uses the operation signals of the first and second microswitches SW1 and SW2 to enable the operation of the X-ray CT apparatus, i.e., photographing operation and enable traveling the X-ray CT apparatus onboard vehicle 1100, i.e., motor vehicle. As shown in FIG. 8, a traveling control circuit 201 outputs a traveling enable signal to an engine starter control circuit 111 of the vehicle 1100 when the first microswitch SW1 is ON and the second microswitch SW2 is OFF. Upon reception of the traveling enable signal, the engine starter control circuit 111 permits activation of the starter, i.e., activation of the engine. In another state, the traveling control circuit 201 outputs a traveling disable signal to the engine starter control circuit 111 of the vehicle. Upon reception of the traveling disable signal, the engine starter control circuit 111 does not permit activation of the starter. Thus, no driving power is supplied to the starter to inhibit activation of the engine.

Figure 9:
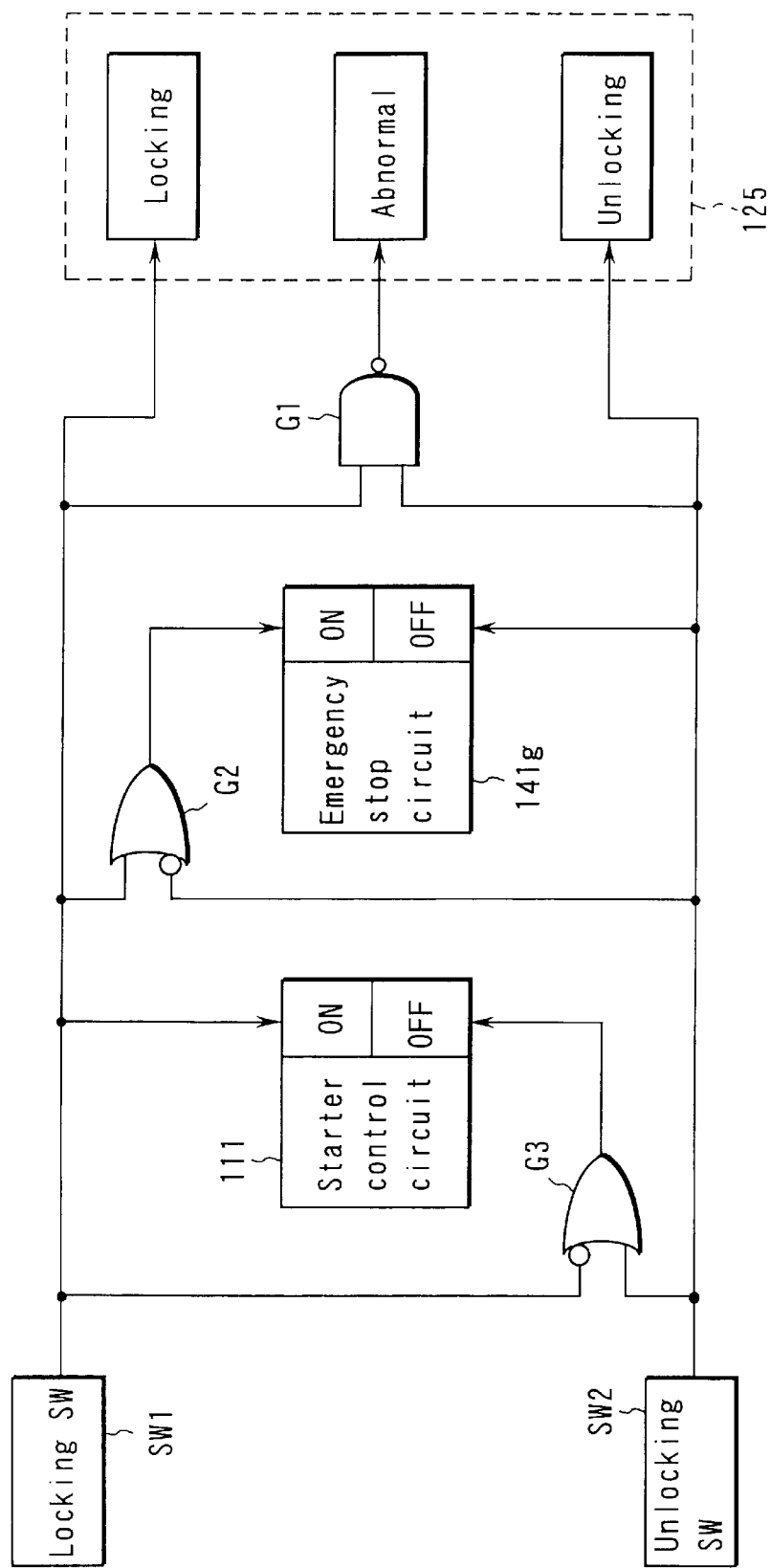
FIG. 9 is a circuit diagram showing part of the traveling control system in FIG. 8.

More specifically, as shown in FIG. 9, a signal from the first microswitch SW1 is supplied to the engine starter control circuit 111 of the motor vehicle and an emergency stop circuit 141g of a controller 141b of the X-ray CT apparatus. For example, if the first microswitch SW1 outputs an ON signal (H level), the starter control circuit 111 is turned on to enable traveling the motor vehicle, and at the same time the emergency stop circuit 141g is turned on via a gate G2 to inhibit photographing operation of the X-ray CT apparatus. If an output from the first microswitch SW1 is an OFF signal (L level), a gate G3 operates to turn off the starter control circuit 111 and inhibit activation of the engine, and the emergency stop circuit 141g is not turned on.

A signal from the second microswitch SW2 is also supplied to the emergency stop circuit 141g of the controller 141b of the X-ray CT apparatus and the engine starter control circuit 111 of the motor vehicle. For example, if the second microswitch SW2 outputs an ON signal (H level), the emergency stop circuit 141g of the X-ray CT apparatus is turned off to normally operate the X-ray CT apparatus, and at the same time the starter control circuit 111 is turned off via the gate G3 to inhibit activation of the motor vehicle. If an output from the second microswitch SW2 is an OFF signal (L level), the gate G2 operates to turn on the emergency stop circuit 141g and inhibit operation of the X-ray CT apparatus, and the starter control circuit 111 is kept off to inhibit activation of the engine of the motor vehicle.

Accordingly, when both the first and second microswitches SW1 and SW2 are OFF, neither the operation of the X-ray CT apparatus nor traveling of the motor vehicle is enabled.

A ring block mechanism for locking the rotating ring to the ring frame 100 when the X-ray CT apparatus onboard vehicle 100 travels and unlocking the rotating ring when the X-ray CT apparatus operates is incorporated in the gantry 121 for the rotating ring to which the X-ray tube and X-ray detector described above are attached to face each other via the photographing port 121a. This ring block mechanism may be a mechanical locking means such as a locking pin & hole structure similar to that of FIG. 7, but may be an electromagnetic brake for applying the brake in the OFF state and releasing the brake in the ON state. In this case, ON/OFF operation is done by operating operation switches on the front cover 121b or performing remote control from the staff room 140. The rotating ring is desirably locked by the protection means at a position where the X-ray tube and X-ray detector attached to the rotating ring so as to face each other become perpendicular to the gantry 121, i.e., almost perpendicular to the floor surface of the motor vehicle 100.

To detect and distinguish the three states of the lock, i.e., the locking state, unlocking state (free rotation state), and intermediate state of the rotating ring, a pair of microswitches SW11 and SW12 are adopted. The traveling control circuit 201 supplies a traveling enable or disable signal to the engine starter control circuit 111 in accordance with the states of the two microswitches SW11 and SW12. The displays 202 and 203 display the locking state.

The bed is provided with a mechanism of locking slide of the top plate and a mechanism of locking elevation of the top plate. The slid locking mechanism and elevation locking mechanism may be mechanical locking means such as a locking pin & hole structure similar to that of FIG. 7, or may be electromagnetic brakes. A pair of microswitches SW21 and SW22 (SW31 and SW32) are employed to detect and distinguish the three states of the lock, i.e., the locking state, unlocking state, and intermediate state of each of slide and elevation. The traveling control circuit 201 supplies a traveling enable or disable signal to the engine starter control circuit 111 in accordance with the states of the pair of microswitches SW21 and SW22 (SW31 and SW32). The displays 202 and 203 display the three, locking, unlocking, and intermediate states so as to distinguish them.

The keyboard and mouse in the CT operation room also comprise locking means, as will be described in detail later. The locking means is typically a rubber band for the keyboard, and a mouse pocket for the mouse. Each switch SW41 is attached to a hook for hanging the rubber band. If the rubber band is hung on the hook via the keyboard, the hook switch SW41 is turned on by the tension. A mouse pocket switch SW51 is attached to the bottom of the mouse pocket. If the mouse is put into the mouse pocket, the mouse pocket switch SW51 is turned by the weight.

The traveling control circuit 201 can determine based on outputs from SW41 and SW51 whether the keyboard and mouse are locked. When the hook switch SW41 is OFF, the traveling control circuit 201 displays on the displays 202 and 203 a message that the keyboard is not locked. When the mouse pocket switch SW51 is OFF, the traveling control circuit 201 displays on the displays 202 and 203 a message that the mouse is not put into the pocket. However, the traveling control circuit 201 does not output any traveling disable signal even if the keyboard is not fixed. Similarly, the traveling control circuit 201 does not output any traveling disable signal even if the mouse is not put into the pocket. This is because even if the keyboard and mouse move during traveling, this does not cause any serious accident, and the user may arbitrarily use another convenient locking means.

Referring back to FIG. 2, the power supply room 130 will be described.

The power supply room 130 is located between the driver's seat 110 and the CT operation room 120, and partially formed from a two-layered structure. A power supply device 131 including a power generator is installed at the lower layer part of the power supply room 130, and an air-cooling system 132 such as a fan for cooling the power supply device 131 is installed at the upper layer part. Since the power supply room 130 has a two-layered structure and the power supply device 131 as a heavy device is arranged at the lower layer part in a direction perpendicular to the longitudinal direction of the motor vehicle, the space efficiency of the motor vehicle increases. Since the power supply room 130 is an independent room, the object in the CT operation room 120 does not feel discomfort due to noise, and the safety also increases.

The power supply room 130 supplies necessary power to the each building device of the X-ray CT apparatus. The space of the power supply room 130 is restricted, a large-size power supply device 131 is difficult to install, and sufficient power cannot always be supplied. For this reason, the X-ray CT apparatus onboard vehicle 100 of the present invention can adjust the load in accordance with the capacity of the power supply device 131, and the adjusting means will be described later.

The staff room 140 formed after the CT operation room 120 will be described. The staff room 140 is mainly used by medical staff such as a doctor and technician in order to operate the X-ray CT apparatus or read and project an acquired CT image. In the staff room 140, the console 141 of the X-ray CT apparatus, a monitor 142 for displaying a CT image, and various devices 143 such as a computer-assisted diagnostic system (lung cancer CAD) 143a for examining a lung cancer, communication system 143b, and analyzer 143c are aligned along one side wall surface of the staff room 140, in other words, along one side wall surface of the motor vehicle in the longitudinal direction.

Figure 10:
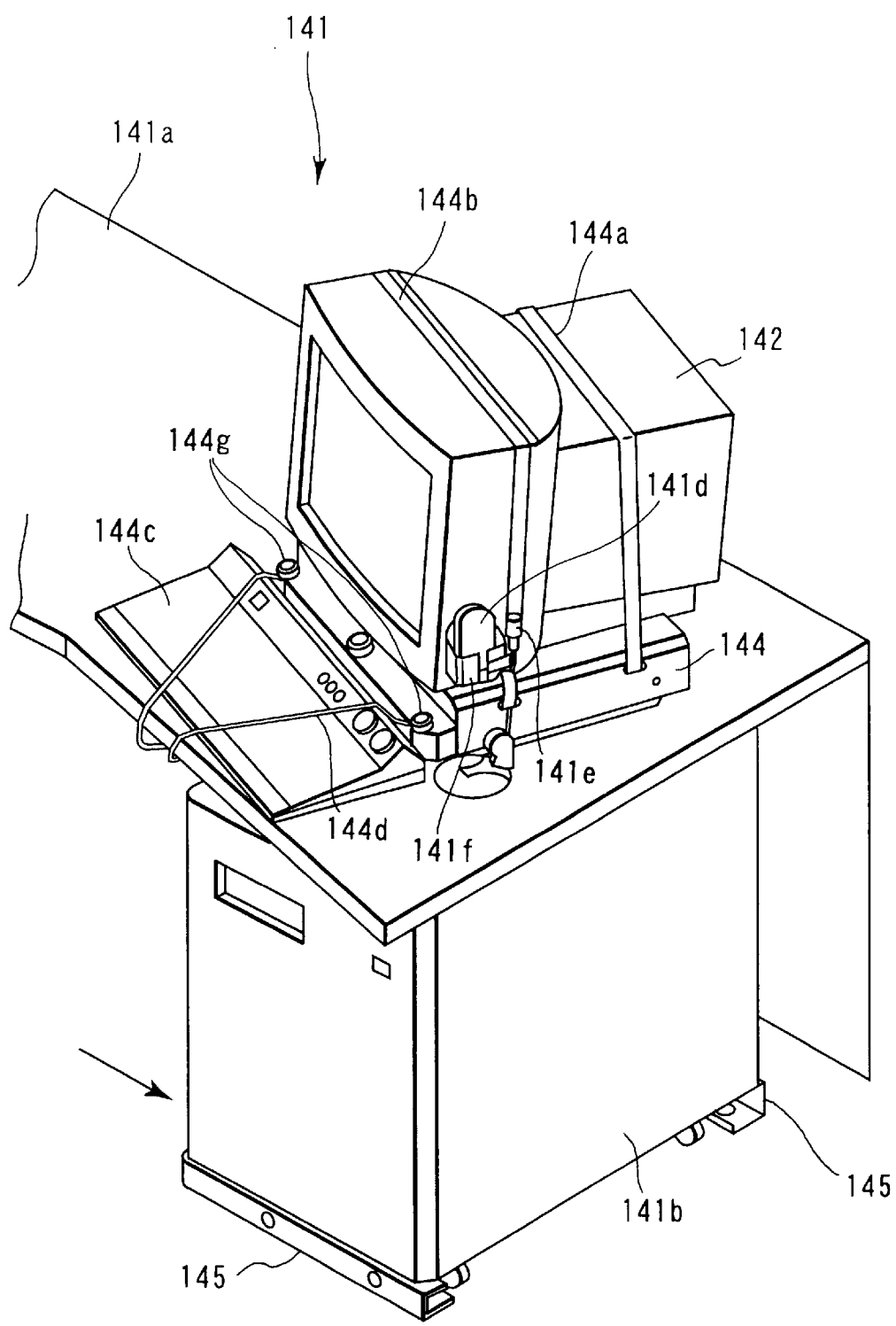
FIG. 10 is a perspective view showing an operation room in FIG. 2.

FIG. 10 is an enlarged view showing the console 141 installed in the staff room 140. The console 141 has a table 141a, a controller 141b below the table 141a, and a keyboard 141c and mouse 141d on the table 141a. The monitor 142 and the monitors of the devices 143 are also located on the table 141a.

Various setting operations of the X-ray CT apparatus, e.g., setting of a tube voltage and tube current for setting the conditions of X-rays emitted from the X-ray tube inside the gantry 121, setting of the slide stroke of the top plate 122a for positioning a portion to be photographed to the photographing port 121a, and setting of the number of shots are designated and input to the controller 141b by the medical staff by using the keyboard 141c and mouse 141d. At this time, the controller 141b determines based on the input tube voltage and tube current whether the load falls within the capacity of the power supply device 131, and if determining that the load exceeds the power supply capacity, outputs a warning to suspend X-ray exposure. If the medical staff changes the settings and the controller 141b determines that the load falls within the power supply capacity, X-rays are normally emitted to acquire CT data.

As described above, the X-ray CT apparatus onboard vehicle 100 supplies power to associated equipment such as the X-ray CT apparatus from the power supply device 131 including the mounted power generator, but the power supply capacity is limited. If X-rays are emitted under the maximum output condition of a general X-ray CT apparatus, the apparatus may be overloaded. If the overloading state repetitively occurs, this may cause the failure of the power supply device 131. Moreover, the power supply may stop to cause the malfunction of the computer or delete acquired important image data. To prevent this, power consumption including power of associated equipment is calculated from necessary power based on X-ray exposure conditions which require the maximum power, and whether the load falls within the capacity of the power supply device 131 is checked.

The monitor 142 is integrally fixed by two rubber bands 144a and 144b to a swing portion 144 fixed to the table 141a rotatably in the horizontal direction. The direction of the monitor 142 can be freely changed together with the swing portion 144 within a predetermined range in the horizontal direction on the table 141a. This can increase the operability in use while protecting the monitor 142 from traveling vibrations.

A microphone 141e for communication between the object under examination in the CT operation room 120 and the medical staff in the staff room 140 is fixed onto the table 141a. When the mouse 141d is not used, it is stored in a mouse pocket 141f fixed to the side surface of the monitor 142, as shown in FIG. 10. The mouse pocket switch SW51 is attached to the bottom of the mouse pocket 141f.

FIG. 10 shows a state wherein the keyboard 141c is fixed by a fixing rubber band 144c interposed between the swing portion 144 and the table 141a when the X-ray CT apparatus onboard vehicle 1100 travels. To operate the X-ray CT apparatus, the rubber band 144c is removed. The rubber band 144c is hung on hooks 144g. The hook switches SW41 are attached to the hooks 144g, and turned on by hanging the rubber band 144c to the hooks 144g via the keyboard 141c. The rubber band 144c has a tension when pulled into an almost V shape, and fixes not only the keyboard 141c but also the monitor 142 together with the swing portion 144 so as to stand traveling vibrations.

Conventionally, when the X-ray CT apparatus onboard vehicle 100 travels, the keyboard 141c and mouse 141d are removed from connectors and stored in a protection case, and when the X-ray CT apparatus is to operate, are connected again, which is cumbersome. However, fixing by the rubber band 144c and storage into the mouse pocket 141f can eliminate cumbersome work and the space of the protection case, thus effectively using the space.

Similar to the monitor 142 and keyboard 141c shown in FIG. 10, the monitors of the devices 143 are attached to swing portions on the table 141a, and their keyboards are also fixed by fixing bands. However, these monitors and keyboards are not illustrated in FIG. 5.

The bottom of the controller 141b below the table 141a is fit in and fixed to two guide plates 145 fixed to the floor of the staff room 140 via rubber vibration insulators. Although not shown, rollers are arranged on the upper surfaces of the guide plates 145.

A sloped base plate attached to the bottom of the controller 141b is slid on the rollers and moved in the direction indicated by the arrow, thereby fitting and fixing the controller 141b at a predetermined position. In maintenance, one side of the controller 141b is lifted to extract the controller 141b to the left (direction opposite to the arrow) in FIG. 10, and the controller 141b, which has a caster at the bottom, can be easily moved to the space left to the table 141a.

The guide plates 145 can fix the controller 141b without projecting from the bottom of the controller 141b, and can contribute to space reduction in the staff room 140.

As shown in FIG. 2, a dressing space 146 is formed along the side wall opposite to the wall along which the devices 143 including the console 141 of the staff room 140 are aligned. A movable shielding member such as a curtain 147 is disposed to partition the dressing space 146 and the devices 143 aligned along the wall surface, as needed. A fixed chair 146a is set in the dressing space 146.

In the staff room 140, the console 141, monitor 142, and devices 143 are aligned along one wall surface. The medical staff can perform work while facing the wall surface and watching the monitor 142 and the screens of the devices 143, and the internal space of the staff room 140 can be widely used. Hence, the staff room 140 can also serve as the dressing room 146, as needed. At this time, the dressing space 146 is shielded from the monitor 142 and devices 143 by the curtain 147 to prevent another object from seeing a diagnostic image and protect the privacy of the object.

The doorway 150 is formed in the back wall of the motor vehicle so as to communicate with the center of the staff room 140. The doorway 150 has steps 151 which are stored in the vehicle when not used.

Figure 11:
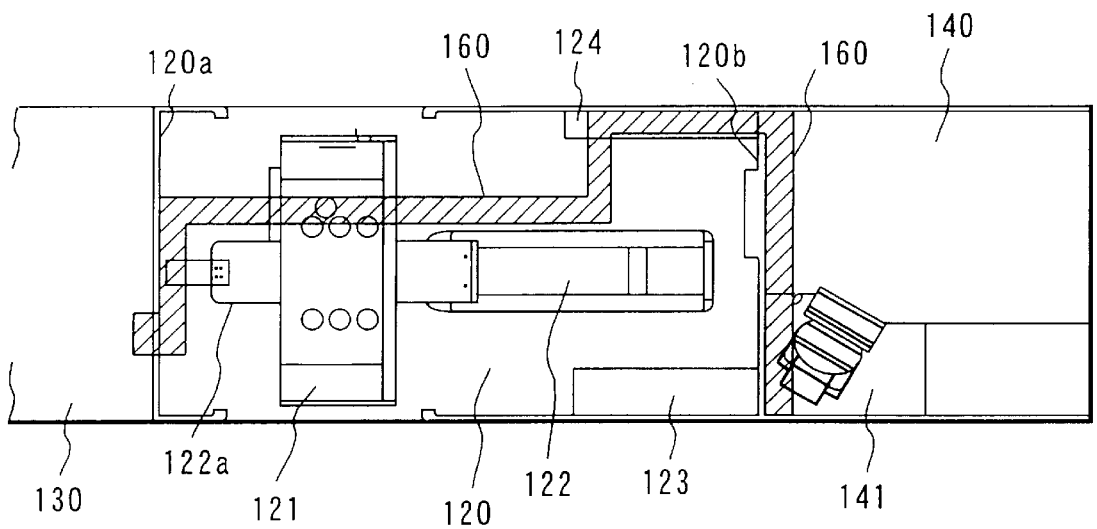
FIG. 11 is a view showing the layout of a pitch below the vehicle floor in FIG. 2.

A pit serving as a layout means for a power supply cable and a cable for connecting the gantry 121 and bed 122 of the X-ray CT apparatus to the console 141 will be explained. FIG. 11 is a view showing a pit formed below the floors of the CT operation room 120 and staff room 140. A hatched portion is a pit 160. The pit 160 extends below the partition wall 120a from the power supply room 130 to the CT operation room 120, is formed along the partition wall 120a, so bends as to extend below the gantry 121, extends straight along the bed 122 so as to detour the rear wheel of the motor vehicle, and further bends to reach the installation position of the switchboard 124. Further, the pit 160 extends below a partition wall 120b between the CT operation room 120 and the staff room 140, and bends to reach the console 141 along the partition wall 120b on the staff room 140 side.

The pit 160 is partitioned into a signal cable space and power supply cable space. The signal cable for exchanging signals between the gantry 121, the bed 122, and the console 141 is stored in the signal cable space of the pit 160. The power supply cable from the power supply device 131 extends through the power supply cable space of the pit 160, temporarily enters the switchboard 124, and extends again from the switchboard 124 through the power supply cable space of the pit 160, thereby supplying power to the gantry 121, bed 122, air-conditioning system 123, console 141, and devices 143.

In this manner, the pit is formed below the floor of the motor vehicle, and stores the signal cable and power supply cable so as to connect devices constituting the X-ray CT apparatus to each other. No portion projects from the floor or wall, which can improve the workability, spatiality, operability, and services. In the conventional X-ray CT apparatus onboard vehicle 1, wiring pits project from the floor and wall to limit the space, obstruct the work of the medical staff, and restrict installation of various devices. However, the X-ray CT apparatus onboard vehicle 100 is free from these problems.

As described in detail above, the present invention employs locking mechanisms for relatively heavy movable portions such as a gantry tilt portion, gantry rotating portion, top plate sliding portion, and bed elevating portion. The states of the locking mechanisms are displayed, and traveling of the vehicle is permitted/inhibited, thereby avoiding an accident such as damage caused by traveling in an unlocking state. When locking of the tilt mechanism by the protection means is reliably released, photographing operation by the x-ray CT apparatus is enabled, and when locking is not released, photographing operation is disabled, thus preventing damage to the tilt mechanism caused by forced operation.

The present invention also employs locking mechanisms for relatively light movable portions such as a keyboard and mouse. The states of the locking mechanisms are displayed to prompt the operator to fix the keyboard and mouse and inform the operator of the possibility of damage caused by a fall. Even if the relatively light movable portions such as the keyboard and mouse are not completely fixed, only these states are notified, and traveling is not inhibited.

Figure 12:
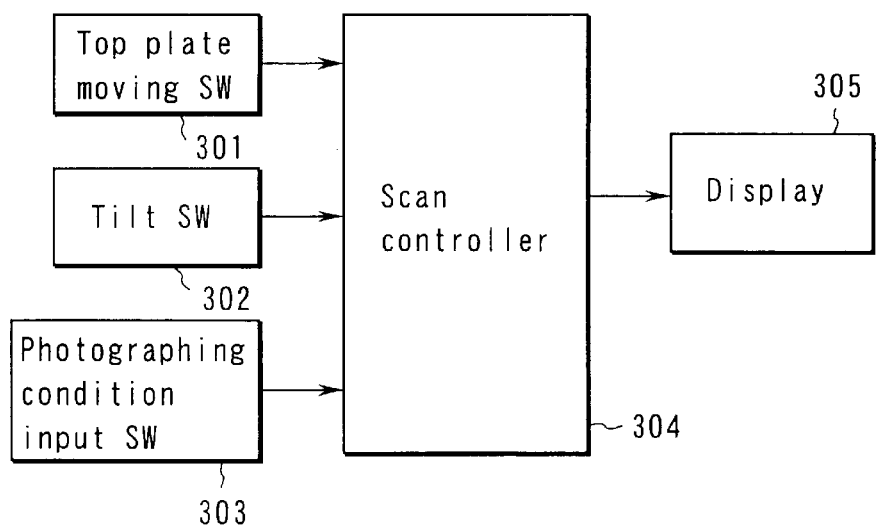
FIG. 12 is a block diagram showing a movable portion control system according to the embodiment of the present invention.

A control function concerning setting of photographing conditions, setting of the gantry tilt angle, and setting of the top plate stroke will be explained with reference to FIGS. 12, 13, and 14. FIG. 4 is an enlarged view showing the gantry 121 and bed 122 installed in the CT operation room 120. The through hole 121a serving as a photographing port is formed at the center of the gantry 121, and the object lying on the top plate 122a of the bed 122 is fed into the photographing port 121a by sliding the top plate 122a.

The slide stroke of the top plate 122a to the photographing port 121a is generally about 1,800 mm at maximum. However, depending on the spatial conditions of the CT operation room 120, e.g., when a satisfactory distance cannot be ensured between the gantry 121 and the partition wall 120a which partitions the CT operation room 120 and power supply room 130, the slide stroke can be appropriately restricted to, e.g., 1,600 mm at maximum by a scan controller 304 in accordance with the distance.

The restriction value is set by changing the slide limit value of the top plate 122a by, e.g., bed control firmware. If the medical staff erroneously designates a slide stroke larger than the limit value via a top plate moving switch 301 in photographing operation, the scan controller 304 determines the designated slide stroke and displays on a display 305 a warning so as to reset the slide stroke. This limit value is definitely discriminated from the movable limit of the slide mechanism of the top plate 122a, and is set shorter than the movable limit on the basis of the spatial conditions of the CT operation room 120. In this sense, the limit value is defined as an allowable limit with respect to the movable limit of the mechanism.

The allowable limit is set with respect to the movable limit so as to prevent the top plate 122a which slides from interfering with the partition wall 120a when the CT operation room 120 is small because the size of the gantry 121 or the like may change depending on the type of motor vehicle or the type of X-ray CT apparatus installed in the CT operation room 120.

Although not shown in the gantry 121, the gantry 121 has the rotating ring to which the X-ray tube and X-ray detector are attached to face each other via the photographing port 121a. The gantry 121 further incorporates a driving unit for driving the rotating ring, a tilt mechanism for tilting the gantry 121, a high-voltage generator for generating a high voltage to be applied to the X-ray tube, and a signal amplifier for amplifying a signal detected by the X-ray detector. The tilt angle of the gantry 121 by the tilt mechanism generally ranges from +30° to −30° (tiltable limit). However, the tilt angle can be properly set to, e.g., +20° to −20° (allowable limit) depending on the spatial conditions of the CT operation room 120, e.g., when the distance between the gantry 121 and the partition wall 120a which partitions the CT operation room 120 and power supply room 130 or the height between the floor and ceiling of the CT operation room 120 cannot be sufficiently ensured in order not to interfere with the ceiling and partition wall 120a of the CT operation room 120 even if a different type of gantry 121 is installed in the CT operation room 120, similar to the bed 122 and top plate 122a. The tilt angle is also set by changing the limit tilt angle of the tilt mechanism by, e.g., tilt mechanism control firmware.

Photographing procedures executed while determining whether the slide stroke of the top plate 122a and the tilt angle of the gantry 121 is proper will be described. Various setting operations of the X-ray CT apparatus, e.g., setting of a tube voltage and tube current for setting the conditions of X-rays emitted from the X-ray tube inside the gantry 121, setting of the slide stroke of the top plate 122a for positioning a portion to be photographed to the photographing port 121a, and setting of the tilt angle and the number of shots are designated and input to the controller 141b by the medical staff by using the switch 301 and switches 302 and 303 such as the keyboard 141c and mouse 141d.

At this time, the controller 141b determines based on the input tube voltage and tube current whether the load does not exceed an allowable limit set lower than the maximum capacity of the power supply device 131 by power consumed by an illumination device, air-conditioning device, and other devices. If the controller 141b determines that the load exceeds the allowable limit, it outputs a warning to suspend x-ray exposure. If the medical staff changes the settings and the controller 141b determines that the X-ray exposure conditions fall within the allowable limit, X-rays are normally emitted to collect CT data.

As described above, the X-ray CT apparatus onboard vehicle 100 supplies power to associated equipment such as the X-ray CT apparatus from the power supply device 131 including the mounted power generator, but the power supply capacity is limited. For example, when the power supply capacity of the power supply device 131 is only 75 kVA, a current which can be supplied to the X-ray CT apparatus is 60 kVA because the air-conditioning system 123 and other associated equipment mounted in the X-ray CT apparatus onboard vehicle 100 require about 15 kVA. However, about 75 kVA is necessary for only the X-ray CT apparatus, but cannot be ensured. For this reason, the tube voltage or current of the X-ray tube in X-ray exposure when the X-ray CT apparatus requires the largest power is restricted to a dedicated allowable limit so as not to exceed the power supply capacity.

When the X-ray exposure condition (tube voltage or current) is set, the power is controlled by calculating a necessary power amount from the set value, and comparing the calculated power amount with an allowable limit obtained by subtracting power necessary for associated equipment from the power supply capacity of the power supply device 131. If X-rays are emitted under the maximum output condition of a general X-ray CT apparatus, the apparatus may be overloaded. If the overloading state repetitively occurs, this may cause the failure of the power supply device 131. Moreover, the power supply may stop to cause the malfunction of the computer or delete acquired important image data. These problems can be solved by the above-described control.

Figure 13:
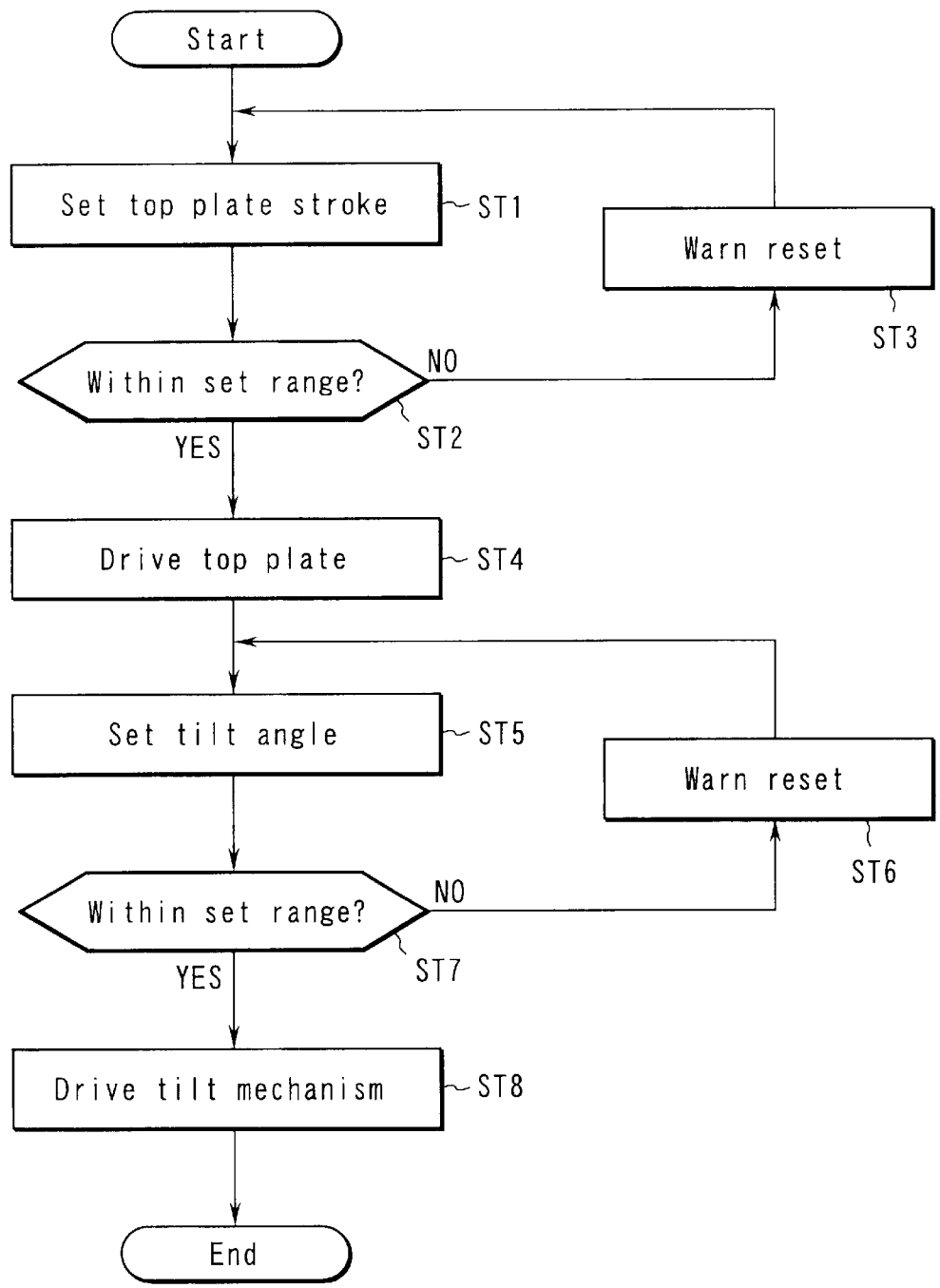
FIG. 13 is a flow chart showing control of a movable portion by a scan controller in FIG. 12.

FIG. 13 is a flow chart showing photographing procedures executed while determining whether the slide stroke of the top plate 122a and the tilt angle of the gantry 121 is proper. Every photographing operation using the X-ray CT apparatus, the medical staff operates the keyboard 141c (switches 301 and 303) to set the slide stroke of the top plate 122a as step 1 (ST1) in accordance with the photographing portion. In ST2, whether the set stroke falls within a predetermined allowable limit is checked, and if YES in ST2, the flow shifts to ST3 to output a warning that the stroke must be reset. In accordance with the warning, the medical staff returns to ST1 to reset the slide stroke of the top plate 122a. If NO in ST2, the flow shifts to ST4 to drive the top plate 122a.

Then, the flow advances to ST5 to set the tilt angle of the gantry 121. Whether the tilt angle set in ST5 falls within a predetermined allowable range is checked in ST7. If NO in ST7, the flow shifts to step ST6 to output a warning that the tilt angle must be reset. In accordance with the warning, the medical staff returns to ST5 to reset the tilt angle. If YES in ST7, the flow advances to ST8 to drive the tilt mechanism, and mechanism setting operation ends.

Figure 14:
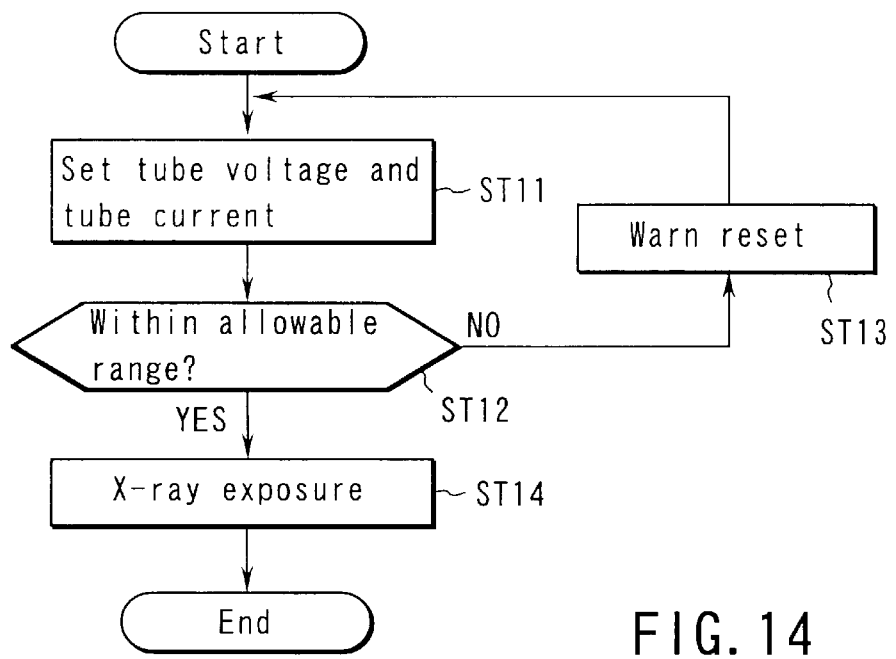
FIG. 14 is a flow chart showing photographing condition control by the scan controller in FIG. 12.

FIG. 14 is a flow chart showing photographing procedures executed while determining whether setting of X-ray exposure conditions (tube voltage and tube current) is proper. X-ray exposure conditions are set in accordance with the photographing portion and the age and obesity of the object. Whether the tube voltage and tube current of the X-ray tube set in step 11 (ST11) fall within an allowable limit set lower than the power supply capacity of the power supply device 131 is determined in ST12. If NO in ST12, the flow shifts to ST13 to output a warning that the tube voltage and tube current must be reset. In accordance with this warning, the medical staff returns to ST11 to reset the tube voltage and tube current. If YES in ST12, the flow shifts to ST14 to permit X-ray exposure.

(Second Embodiment)

Figure 15:
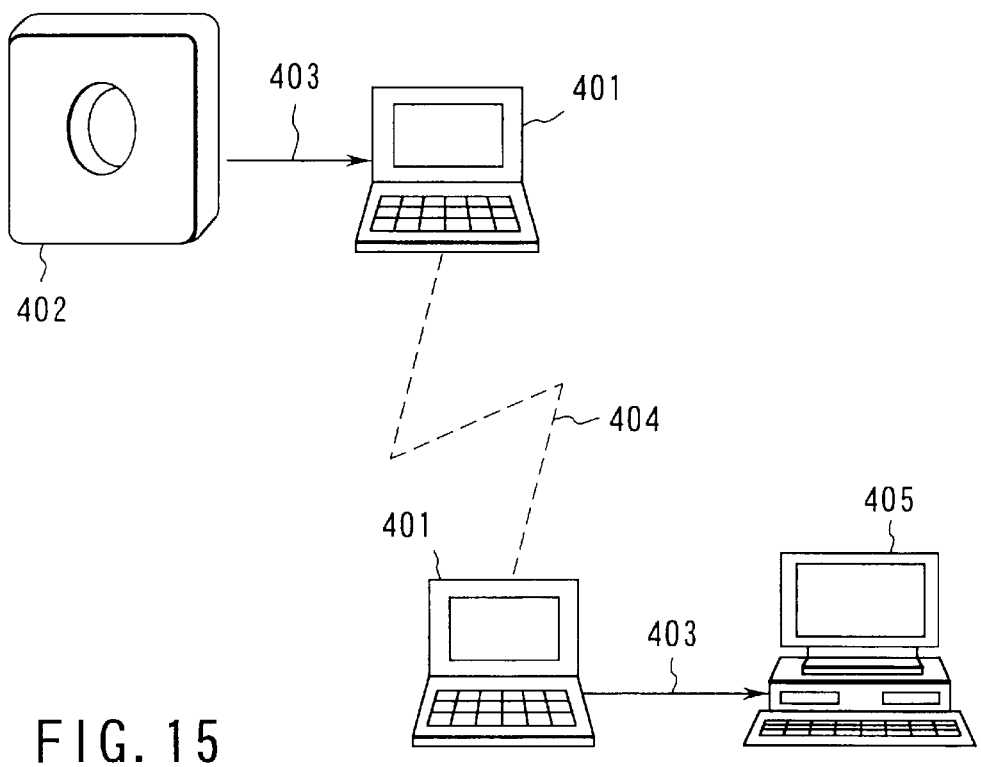
FIG. 15 is a view for explaining a medical image information transfer method according to another embodiment of the present invention.

An embodiment of a medical image information transfer method and apparatus according to the present invention will be described in detail with reference to FIG. 15. As a means for implementing this embodiment, a mobile personal computer called a commercially available notebook type personal computer, or a mobile work station (to be simply referred to as a mobile WS hereinafter) is prepared. A mobile WS 401 incorporates a hard disk having a memory capacity of about 10 GB, and a hard disk can be properly added. The mobile WS 401 can realize a much larger memory capacity than an existing CD-R or 3.5" magneto-optic disk, and can record necessary medical image information acquired from about 200 objects (i.e., medical image information of 200 samples) in group examination.

The mobile WS 401 incorporates a DICOM STORAGE SCP (SCP; Service Class Provider) function and DICOM STORAGE SCU (SCU; Service Class User) function as an Ethernet interface and application software in order to enable DICOM communication. DICOM STORAGE SCP defines functions which should be held on a medical image reception side in saving medical image information defined by DICOM. Similarly, DICOM STORAGE SCU defines functions which should be held on a medical image transmission side in saving medical image information.

A modality device 402 incorporates the DICOM STORAGE SCU function. The mobile WS 401 is set near the modality device 402 and connected to it via a signal line (e.g., Ethernet) 403. With this arrangement, medical image information acquired by the modality device 402 is transferred to the mobile WS 401 via the signal line 403 and stored in the hard disk of the mobile WS 401. That is, the mobile WS 401 functions as an image server device for temporarily saving medical image information.

The mobile WS 401 which temporarily stores medical image information is moved close to an image server device 405 by a proper carrier means 404. For example, when the mobile WS 401 and modality device 402 are mounted in an examination vehicle (not shown), the medical staff may carry the mobile WS 401 to the installation place of the image server device 405 after the examination vehicle comes back to a hospital as a base, or the carrier person may carry the mobile WS 401 from a group examination place to a predetermined hospital.

The mobile WS 401 is connected via the signal line 403 to the image server device 405 installed in the predetermined hospital. The medical image information which has been acquired by the modality device 402 and temporarily stored in the mobile WS 401 is transferred by offline to the image server device 405. Transfer operation from the mobile WS 401 to the image server device 405 may be performed automatically or manually. Also, the image server device 405 must incorporate the DICOM STORAGE SCP function.

The medical image information transferred to the image server device 405 is displayed on an image diagnostic apparatus (not shown), and diagnosed by a medical specialist. If necessary, the medical image information stored in the image server device 405 can be properly read out.

According to the second embodiment, the DICOM STORAGE SCU function is requested of the modality device 402, and the DICOM STORAGE SCP function is requested of the image server device 405. The mobile WS 401 having both the DICOM STORAGE SCU function and DICOM STORAGE SCP function is interposed between the modality device 402 and the image server device 405. This can greatly improve connectivity even in the environment where the modality device 402 and image server device 405 cannot be connected by a signal line under physical restrictions.

The mobile WS 401 incorporates a hard disk having a storage capacity of about 10 GB, so that the storage capacity of medical image information is much larger than a magneto-optic disk or CD-R. One mobile WS 401 can save all pieces of medical image information collected by one-day group examination by temporarily recording pieces of medical image information acquired by group examination objected to many objects, on the mobile WS 401 instead of an information recording medium such as a 3.5" magneto-optic disk or CD-R.

As described in detail above, according to the second embodiment, the connectivity between the modality device and the image server device can be greatly improved even in the environment where the modality device and image server device cannot be connected by a signal line under physical restrictions.

One mobile WS 401 can save all pieces of medical image information acquired by one-day group examination by temporarily recording pieces of medical image information acquired by group examination on the mobile WS 401. Unlike the prior art, the operator need not frequently exchange information recording media such as 3.5" magneto-optic disks or CD-Rs, which increases the efficiency and reduces the burden on the operator such as medical staff.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT apparatus which can be mounted in a motor vehicle, trailer, or container, comprising:
   a locking mechanism unit for locking at least one of movable portions of the X-ray CT apparatus;
   detectors for detecting locking/unlocking states of said locking mechanism unit; and
   a notifying unit for representing the states of said locking mechanism unit on the basis of outputs from said detectors.

2. An apparatus according to claim 1, wherein said locking mechanism unit includes a plurality of locking mechanisms, said locking mechanisms are attached to a gantry tilt mechanism of the X-ray CT apparatus, a gantry rotating mechanism, a top plate slide mechanism of a bed, and an elevation mechanism of the bed.

3. An apparatus according to claim 2, wherein said locking mechanism of the gantry tilt mechanism locks a gantry to a position where a tilt angle is 0°.

4. An apparatus according to claim 1, wherein said locking mechanism unit includes a plurality of locking mechanisms, said detectors have switches for detecting the locking states of said locking mechanisms, and switches for detecting unlocking states of said locking mechanisms.

5. An apparatus according to claim 4, wherein said notifying unit distinguishes and represents a locking state, unlocking state, or intermediate state of each locking mechanism.

6. An apparatus according to claim 4, further comprising an output unit for outputting a photographing inhibit signal when even one locking mechanism is not in the unlocking state.

7. A motor vehicle which contains an X-ray CT apparatus defined in claim 1, comprising:
   a traveling driving unit;
   a starter of said traveling driving unit; and
   a control circuit of said starter,
   wherein said locking mechanism unit includes a plurality of locking mechanisms, said control circuit controls said starter so as not to activate said traveling driving unit when even one locking mechanism is not in the locking state.

8. A vehicle according to claim 7, further comprising displays respectively installed in a traveling driver's seat and a CT operation room to display states of said locking mechanisms.

9. An X-ray CT apparatus which can be mounted in a motor vehicle, trailer, or container, comprising:

locking mechanisms for locking at least some of movable portions of the X-ray CT apparatus;

detectors for detecting locking states of said locking mechanisms; and an output unit for outputting a moving inhibit signal when even one locking mechanism is not in the locking state.

10. A motor vehicle which contains an X-ray CT apparatus defined in claim 9, comprising:

a traveling driving unit;

a starter of said traveling driving unit; and a control circuit of said starter, wherein said control circuit controls said starter so as not to activate said traveling driving unit in accordance with a moving inhibit signal.

11. An X-ray CT apparatus which is mounted in a motor vehicle, trailer, or container, comprising:

locking mechanisms for respectively locking gantry rotation of the X-ray CT apparatus, gantry tilt, top plate slide of a bed, elevation of the bed, a keyboard, and a mouse;

detectors for detecting locking/unlocking states of said locking mechanisms;

a display for displaying the states of all said locking mechanisms on the basis of outputs from said detectors; and an output unit for outputting a moving inhibit signal on the basis of outputs from said detectors when even one of said locking mechanisms for gantry rotation, gantry tilt, top plate slide of the bed, and elevation of the bed is not locked.

12. A motor vehicle which contains an X-ray CT apparatus defined in claim 11, comprising:

a traveling driving unit;

a starter of said traveling driving unit; and a control circuit of said starter, wherein said control circuit controls said starter so as not to activate said traveling driving unit in accordance with a moving inhibit signal.

13. A vehicle according to claim 12, further comprising displays respectively installed in a traveling driver's seat and a CT operation room to display the states of said locking mechanisms.

14. An X-ray CT apparatus which can be mounted in a motor vehicle, trailer, or container, comprising:

an input device for inputting a gantry tilt angle of the X-ray CT apparatus and a top plate slide distance of a bed; and an output unit for outputting a message which prompts re-input of the gantry tilt angle when the input gantry tilt angle exceeds an allowable limit set smaller than a tiltable limit of a tilt mechanism, and outputting a message which prompts re-input of the top plate slide distance when the input top plate slide distance exceeds an allowable limit set shorter than a movable limit of a slide mechanism.

15. An X-ray CT apparatus which can be mounted in a motor vehicle, trailer, or container, comprising:

an input device for inputting a gantry tilt angle of the X-ray CT apparatus; and an output unit for outputting a message which prompts re-input of the gantry tilt angle when the input gantry tilt angle exceeds an allowable limit set smaller than a tiltable limit of a tilt mechanism.

16. An x-ray CT apparatus which can be mounted in a motor vehicle, trailer, or container, comprising:

an input device for inputting a top plate slide distance of a bed; and an output unit for outputting a message which prompts re-input of the top plate slide distance when the input top plate slide distance exceeds an allowable limit set shorter than a movable limit of a slide mechanism.

17. An X-ray CT apparatus which can be mounted in a motor vehicle, trailer, or container, comprising:

an input device for inputting an exposure condition of the X-ray CT apparatus; and an output unit for outputting a message which prompts re-input of the exposure condition when power consumption corresponding to the exposure condition exceeds an allowable limit set smaller than a maximum capacity of a power supply device.

18. An apparatus according to claim 17, wherein said output portion outputs a message which prompts re-input of a tube current and/or tube voltage.

19. A motor vehicle which contains an X-ray CT apparatus, comprising:

locking mechanisms for locking at least some of movable portions of the X-ray CT apparatus;

detectors for detecting locking/unlocking states of said locking mechanisms; and a notifying unit for representing the states of said locking mechanisms on the basis of outputs from said detectors.

20. A trailer which contains an X-ray CT apparatus, comprising:

locking mechanisms for locking at least some of movable portions of the X-ray CT apparatus;

detectors for detecting locking/unlocking states of said locking mechanisms; and a notifying unit for representing the states of said locking mechanisms on the basis of outputs from said detectors.

21. A container which contains an X-ray CT apparatus, comprising:

locking mechanisms for locking at least some of movable portions of the X-ray CT apparatus;

detectors for detecting locking states of said locking mechanisms; and a notifying unit for representing the states of said locking mechanisms on the basis of outputs from said detectors.

* * * * *